United States Patent [19]

Hasegawa et al.

[11] Patent Number: 5,043,407

[45] Date of Patent: Aug. 27, 1991

[54] HYDROPHILIC FINE GEL PARTICLES AND PROCESS FOR PRODUCTION THEREOF

[75] Inventors: Jun Hasegawa, Kamakura; Haruki Oikawa, Yokohama; Osamu Kobayashi, Yokohama; Yasuo Kataoka, Yokohama; Masayoshi Sekiya, Tokyo, all of Japan

[73] Assignee: Nippon Zeon Co., Ltd., Tokyo, Japan

[21] Appl. No.: 556,366

[22] Filed: Jul. 24, 1990

Related U.S. Application Data

[62] Division of Ser. No. 329,567, Mar. 28, 1989, Pat. No. 4,988,568.

[30] Foreign Application Priority Data

Mar. 30, 1988 [JP] Japan .................... 63-77910

[51] Int. Cl.$^5$ ........................................... C08F 226/02
[52] U.S. Cl. ................................................. 526/307.6
[58] Field of Search ..................................... 526/307.6

[56] References Cited

U.S. PATENT DOCUMENTS

| | | | |
|---|---|---|---|
| 3,336,269 | 8/1967 | Monagle | 526/307.6 |
| 3,509,113 | 4/1970 | Monagle et al. | 526/307.6 |
| 3,711,574 | 1/1973 | Jaworek et al. | |
| 3,929,739 | 12/1975 | Barabas et al. | |
| 3,968,306 | 7/1976 | Yoshihara et al. | 526/307.6 |
| 4,070,348 | 1/1978 | Kraemer et al. | 526/307.7 |
| 4,511,694 | 4/1985 | Krämer et al. | 526/212 |
| 4,722,958 | 2/1988 | Sauer et al. | |
| 4,748,220 | 5/1988 | Hartmann et al. | |
| 4,950,725 | 8/1990 | Flesher et al. | 526/307.6 |

FOREIGN PATENT DOCUMENTS 0207714  1/1987  European Pat. Off. .......... 526/307.6

OTHER PUBLICATIONS

"Particle Size Control in Dispersion Polymerization of Polystyrene", Can. J. Chem., vol. 63, 1985, pp. 209–216.

Primary Examiner—Joseph L. Schofer
Assistant Examiner—N. Sarofin
Attorney, Agent, or Firm—Sherman & Shalloway

[57] ABSTRACT

Hydrophilic fine gel particles, said particles being crosslinked polymer particles comprising 20–94.8% by weight of a monoethylenically unsaturated amide monomer, 5–60.0% by weight of a crosslinkable ethylenically unsaturated monomer, 0.1–30% by weight of an ethylenically unsaturated carboxylic acid, 0.1–50% by weight of an ester monomer of an acrylic or methacrylic acid, and 0–30% by weight of a monomer copolymerizable with the above-mentioned monomers, said particles having a particle diameter in a waterswollen state of 0.1–10 μm and a weight-average particle diameter/number-average particle diameter ratio of 1.2 or less; and a process for producing hydrophilic fine gel particles having a particle diameter in a water-swollen state of 0.1–10 μm and a weight-average particle diameter/number-average particle diameter ratio of 1.2 or less, which comprises copolymerizing a monomer mixture of 20–94.8% by weight of a monoethylenically unsaturated amide monomer, 5–60.0% by weight of a crosslinkable ethylenically unsaturated monomer, 0.1–30% by weight of an ethylenically unsaturated carboxylic acid, 0.1–50% by weight of an ester monomer of an acrylic or methacrylic acid, and 0–30% by weight of a monomer copolymerizable with the above-mentioned monomers using a radical polymerization initiator in a solvent which dissolves these monomers but does not dissolve the resulting polymer.

5 Claims, No Drawings

HYDROPHILIC FINE GEL PARTICLES AND PROCESS FOR PRODUCTION THEREOF

This is a division of application Ser. No. 329,567, filed Mar. 28, 1989, now U.S. Pat. No. 4,988,568

FIELD OF INDUSTRIAL APPLICATION

This invention relates to hydrophilic fine gel particles having a narrow particle diameter distribution and a process for the production thereof.

PRIOR ARTS

With the growth of the biological industry, hydrophilic fine gel particles have been increasingly used in recent years. For example, they have been used as carrier particles for enzyme immobilization, particles for column in chromatography for separation of giant molecules such as biopolymers, or carrier particles for diagnostic medicines in the particle agglutination reaction in which there is utilized biological reaction such as antigen-antibody reaction.

As hydrophilic fine gel particles, there have hitherto been those resulting from insolubilizing natural polymers such as dextran, agarose and gelatine using various crosslinking agents, or those resulting from polymerizing acrylamide together with a crosslinking agent. These processes for the production of the particles have been known. In case of dextran gel, for example, an alkali solution of dextran having a proper molecular-weight distribution is dispersed in a proper organic solvent immiscible with water, then a dispersion stabilizer such as a nonionic surface active agent is added to the dispersion to form a water-in-oil type dextran emulsion. Epichlorohydrin is added to the system to react it with the dextran matrix to thereby form glyceric crosslinkages between saccharic chains, thus giving gel particles. Further, polyacrylamide gel, which is a synthetic polymer, is produced by the so-called inverse suspension polymerization such as those disclosed in Japanese Patent Publication No. 25921/1981 corresponding to DE-2237316, FR-2194726, GB-1431946 and U.S. Pat. No. 4,070,348), Japanese Laid-open Patent Application No. 153010/1982 (corresponding to DE-3106456, DE-3168696G, EP-74822E, U.S. Pat. No. 4,511,694 and CA-1202748), etc., or by grinding and classifying a polymer mass resulting from polymerization in a solution. In these processes, the particle diameter, particle diameter distribution and particle shape of the resulting particles depend upon conditions of mechanical stirring at the time when monomers are suspended or conditions of grinding the polymer mass. Usually, the particles have a particle diameter of at least several ten microns. The overall surface area of the particles is small, and the particle diameter distribution of the particles is wide. These particles as above, when used as carrier particles for diagnostic medicines or the like as mentioned above, fail to be sufficient in respect of reaction efficiency, reaction reproducibility or sensitivity.

Further, since these fine gel particles have therein natural polymers as a polymeric skeleton, it is almost impossible to control the colloidal properties desired by the users of the particles such as types and amounts of functional groups or potential. This raises the problem that there is a limit to a method of immobilizing biologically active substances to these hydrophilic gel particles.

Furthermore, as a process which overcomes the above-mentioned defect, there has recently been proposed a process for producing hydrophilic particles which comprises forming polymer particles using more than 50% glycidyl methacrylate and then carrying out ring opening of epoxy groups by use of an acid or a base to convert them into 2,3-dioxypropyl methacrylate units (Japanese Patent Publication No. 29962/1983). However, use of the particles produced by this process for treating proteins such as enzymes, antigens and antibodies involves modification of the proteins unless the acid or base used in the ring opening of the epoxy groups are thoroughly removed by sufficient purification. Further, when hydrophilic particles are used as carrier particles for diagnostic medicines, particles for column in chromatography or carrier particles for enzyme immobilization, since portions participating in the reaction are surfaces of the particles, usually, the inside of the particles does not need to be hydrophilic. In case of the hydrophilic particles produced by the above process, however, epoxy groups are introduced into the inside of the particles as well, it is necessary to use glycidyl methacrylate in a great amount. Furthermore, since the hydrophilic particles produced by the above process have a wide particle diameter distribution though they have a particle diameter of a micron order, they are not enough to meet the required fundamental efficiency such as sufficient reaction sensitivity or the like.

PROBLEMS WHICH THIS INVENTION IS INTENDED TO SOLVE

It is an object of this invention to provide hydrophilic fine gel particles free of the above defects.

After strenuous efforts of investigation to achieve the above object, the inventors of this application have discovered that by polymerizing a specific monomer mixture by dispersion polymerization, there can be obtained hydrophilic fine gel particles having a particle diameter in a water-swollen state of 0.1-10 $\mu$m and a sharp particle diameter distribution. (Means of solving the problems)

Thus, according to this invention, there are provided

[1] hydrophilic fine gel particles, said particles being crosslinked polymer particles comprising 20-94.8% by weight of a monoethylenically unsaturated amide monomer, 5-60.0% by weight of a crosslinkable ethylenically unsaturated monomer, 0.1-30% by weight of an ethylenically unsaturated carboxylic acid, 0.1-50% by weight of an ester monomer of an acrylic or methacrylic acid, and 0-30% by weight of a monomer copolymerizable with the above-mentioned monomers, said particles having a particle diameter in a water-swollen state of 0.1-10 $\mu$m and a weight-average particle diameter/number-average particle diameter ratio of 1.2 or less, and

[2] a process for producing hydrophilic fine gel particles having a particle diameter in a water-swollen state of 0.1-10 $\mu$m and a weight-average particle diameter/number-average particle diameter ratio of 1.2 or less, which comprises copolymerizing a monomer mixture of 20-94.8% by weight of a monoethylenically unsaturated amide monomer, 5-60.0% by weight of a crosslinkable ethylenically unsaturated monomer, 0.1-30% by weight of an ethylenically unsaturated carboxylic acid, 0.1-50% by weight of an ester monomer of an acrylic or methacrylic acid, and 0-30% by weight of a monomer copolymerizable with the above-mentioned monomers using a radical polymerization initiator in a solvent which dissolves these monomers but does not dissolve the resulting polymer.

The hydrophilic fine gel particles of this invention are produced by dispersion polymerization. The dispersion polymerization [see, for example, CAN. J. Chem., vol. 63,209-216 (1985)] is a method of polymerizing monomers in an organic solvent which dissolves the monomers but does not dissolve the resulting polymer using a polymerization initiator which is soluble in said solvent. In order to prevent coagulation of the resulting polymer, a dispersion stabilizer is added, as required, to the reaction system. The mechanism of the polymerization has not yet been made clear. It is presumed that when the polymerization degree of the polymer formed by polymerization reaction in the solution has reached to a certain level, said polymer precipitates in the form of particles and subsequently the polymerization reaction heterogeneously proceeds. Observation on the behavior of the polymerization is that the transparent reaction system assumes a milk-white color in several minutes after initiation of the polymerization. Since the whole of the polymer precipitates almost at the same time, there can be obtained particles having a uniform particle diameter.

Of the monomers used in this invention, the monoethylenically unsaturated amide monomer is a monomer forming the skeleton of the hydrophilic fine gel particles of this invention and an ingredient essential for imparting hydrophilicity to the particles. Examples of the monoethylenically unsaturated amide monomer may include acrylamide, methacrylamide, diacetone acrylamide, N-hydroxymethyl acrylamide, etc. These monomers may be used singly or in a combination of two or more of them. The monoethylenically unsaturated amide monomers are usually used in an amount of 20-94.8% by weight of all of the monomers. If they are used in an amount of less than 20% by weight, the resulting particles will not be fit for the object of this invention. If they are used in an amount more than 94.8% by weight, it will be difficult to insolubilize the resulting polymer particles and to control the particle diameter, and the amount of functional groups in the polymer will be insufficient. Preferably, said monomers are used in an amount of 20-88% by weight.

The crosslinkable ethylenically unsaturated monomer used in this invention is an ingredient essential for insolubilizing the particles and rendering the particles water-swellable. Examples of the crosslinkable ethylenically unsaturated monomer may include bis(meth)acrylamide monomers such as methylene-bis(meth)acrylamide; poly(meth)acrylate esters of polyhydric alcohols such as ethylene glycol di(meth)acrylate, triethylene glycol dimethacrylate, ethylene dimethacrylate, trimethylolpropane trimethacrylate; etc. The crosslinkable ethylenically unsaturated monomers are used in an amount of 5-60% by weight of all of the monomers. If they are used in an amount of less than 5% by weight, there cannot be obtained gel particles having good water-swellability. If they are used in an amount of more than 60% by weight, the monodispersibility of the particle diameter distribution will be impaired (a weight-average particle diameter/number-average particle diameter ratio will be more than 1.2). Preferably, said monomers are used in an amount of 10-50% by weight.

The ethylenically unsaturated carboxylic acid used in this invention is an ingredient essential for retaining the monodispersibility of the particle diameter distribution, and there cannot be obtained monodisperse particles from polymerization carried out in the absence of said acid. Examples of the ethylenically unsaturated carboxylic acid may include acrylic acid, methacrylic acid, crotonic acid, cinnamic acid, itaconic acid, fumaric acid, maleic acid, butenetricarboxylic acid, 3-butenoic acid, 4-pentenoic acid, etc. Said carboxylic acids are used in an amount of 0.1-30% by weight of all of the monomers. If they are used in an amount of more than 30% by weight, the resulting particles will have a wide particle diameter distribution. Preferably, said acids are used in an amount of 2-20% by weight.

The ester of acrylic or methacrylic acid used in this invention is an ingredient essential for introducing specific functional groups into the resulting particles and retaining the monodispersibility of said particles. The (meth)acrylic acid ester monomer is a mono(meth)acrylate ester, and specific examples of said ester may include ethylene oxide-containing (meth)acrylic acid ester such as ethylene glycol (meth)acrylate or triethylene glycol (meth)acrylate; hydroxy group-containing (meth)acrylic acid ester such as hydroxymethyl (meth)acrylate or hydroxypropyl (meth)acrylate; epoxy group-containing (meth)acrylic acid ester such as glycidyl (meth)acrylate; amino group-containing (meth)acrylic acid ester such as methylaminoethyl (meth)acrylate, t-butylaminoethyl (meth)acrylate, dimethylaminoethyl (meth)acrylate, dimethylaminopropyl (meth)acrylate, diethylaminoethyl (meth)acrylate or dibutylaminoethyl (meth)acrylate, and alkyl (meth)acrylic acid ester such as methyl (meth)acrylate, ethyl (meth)acrylate or butyl (meth)acrylate. These monomers may be used singly or in a combination of two or more of them. The amounts of the monomers to be used need to be regulated according to the purpose for which the particles are used. In order to retain the monodispersibility of the particles, said monomers are used in an amount of 0.1-50% by weight, preferably 5-40% by weight, of all of the monomers.

The other copolymerizable monomers optionally used in this invention are used for adjusting the hydrophilicity or water-swellability of the particles. Examples of these monomers may include aromatic vinyl monomers such as styrene, alpha-methylstyrene, p-methylstyrene, chloromethylstyrene or halogenated styrene; and conjugated diolefins such as butadiene or isoprene. Monomers other than those mentioned above may also be used as far as they are soluble in the solvent used in the polymerization reaction and copolymerizable with the other monomer ingredients forming the particles. These monomers are used in an amount of 0-30% by weight of all of the monomers. If these monomers are used in an amount of more than 30% by weight, the proportions of the other ingredients forming the particles will decline, and the particle diameter distribution of the swollen particles will become wider.

No particular restrictions are placed on the solvent used in this invention, and any solvents may be used as far as they dissolve the polymerization initiator and monomers but do not dissolve the resulting polymer. Specific examples of the solvent may include lower alcohols, tetrahydrofuran, dimethylformamide, dioxane, methyl ethyl ketone, pyridine, dimethylsulfoxide, etc. The above-mentioned solvents may be mixed with water as required. Lower alcohols are especially preferred. The lower alcohols are alcohols having 6 carbon atoms at most, and specific examples of the alcohol may include methyl alcohol, ethyl alcohol, propyl alcohols, butyl alcohols, etc. These alcohols may also be used in combination of two or more of them.

Preferably, the concentration of the monomers in the reaction solution at the time of initiation of the reaction is 50% by weight or less. If the concentration is more than 50% by weight, the particles will agglutinate to thereby make it difficult to obtain particles as primary particles. More preferably, the concentration is 1–20% by weight.

In this invention, as the radical polymerization initiator, there are used hitherto known azo compounds, organic peroxides, etc., but no particular restrictions are placed on said radical polymerization initiator. Any radical polymerization initiators may be used as far as they are soluble in the above-mentioned solvents. For example, as the azo compounds, there may be mentioned 2,2-azobisisobutyronitrile, 2,2-azobis(2-methyl)-valeronitrile, etc. As the organic peroxides, there may be mentioned acetyl peroxide, propionyl peroxide, isobutyryl peroxide, benzoyl peroxide, etc. These compounds may also be used in a suitable combination. No particular restrictions are placed on the amount of said initiator to be used. The amount varies with a type of said initiator, and said initiator is usually used in an amount of 0.005–5 parts by weight per 100 parts of the momomer mixture.

The polymerization temperature, which varies with a type of the solvent to be used and a type of the radical polymerization initiator to be used, is desirably within a range of usually 20°–100° C.

Thus, by carrying out dispersion polymerization of the above-mentioned monomers, there can be obtained hydrophilic fine gel particles having a particle diameter in a water-swollen state of 0.1–10 μm and a sharp particle diameter distribution (a weight-average particle diameter/number-average particle diameter ratio ≦1.2).

The particles obtained by the polymerization are separated from the polymerization reaction solution by usual operation of separation such as filtration, decantation, evaporation, etc.

Usually, the polymerization is carried out by putting en bloc all of the monomers to be used into a reactor together with the polymerization initiator and solvent. The polymerization may also be carried out by first polymerizing part of the monomers and then adding thereto the remainder of the monomers together with the polymerization initiator or together with the polymerization initiator and solvent as required. In the above case as well, the concentration of the monomers in the reaction solution is preferably 50% by weight or less for the reasons mentioned above. (Effect of the invention)

Thus, according to this invention, there can be obtained hydrophilic fine gel particles having a particle diameter in a water-swollen state, particle diameter distribution, types and amounts of their functional groups as well as crosslink density controlled as compared with hitherto known hydrophilic fine gel particles. These hydrophilic fine gel particles can be used as carrier particles for diagnostic medicines. (Examples)

With reference to examples, this invention will be more specifically described below. In the examples, parts and percentages are those by weight unless otherwise specified.

In these examples, the particle diameter in a water-swollen state of the hydrophilic fine gel particles was measured by means of a Coulter multisizer (a product of Coulter Electronics, Inc.), and the ζ-potential thereof was measured by means of a microscope-type electrophoretic velocity measuring equipment (a product of Rank Brothers, Ltd.; Mark II Electrophoresis Measuring Equipment).

EXAMPLE 1

The inside of a 2 liter-reactor provided with an agitating blade, a condenser, a nitrogen gas inlet tube and a thermometer was beforehand purged with a nitrogen gas. The reactor was charged with 750 g of ethanol, 67.1 g of acrylamide, 10 g of glycidyl methacrylate (BLENMER G produced by Nippon Oil and Fats Co., Ltd.), 16.2 g of methylene-bisacrylamide, 10 g of methacrylic acid and 0.42 g of 2,2-azobisisobutylonitrile, and agitation was carried out till the system became uniform. Then, the system was heated to 60° C. with nitrogen bubbling to allow the system to initiate reaction. The reaction system was retained as it was for 24 hours, and then the reaction system was cooled. The ethanol was removed from the resulting suspension by means of an evaporator. The suspension was further treated in a vacuum dryer for 12 hours to thoroughly remove the ethanol to thereby give hydrophilic fine gel particles. The particles were added to distilled water, and a 0.1N aqueous solution of NaOH was added to the resulting suspension till the pH value of the suspension became 9 to swell the fine gel particles.

The hydrophilic fine gel particles so obtained were spherical particles having a weight-average particle diameter in a water-swollen state of 2.05 μm, a number average particle diameter of 1.82 μm and a very sharp particle diameter distribution (a weight-average particle diameter/number-average particle diameter ratio = 1.13). The ζ-potential of the particles was −32.5 mV in distilled water.

COMPARATIVE EXAMPLE 1

Polymerization reaction was carried out in the same manner as in Example 1 except that methacrylic acid was not used.

The hydrophilic fine gel particles so obtained were spherical particles having a weight-average particle diameter in a water-swollen state of 4.85 μm, a number-average particle diameter of 1.32 μm and a very wide particle diameter distribution (a weight-average particle diameter/number-average particle diameter ratio = 3.67).

EXAMPLE 2

Polymerization was carried out in the same manner as in Example 1. After conclusion of the polymerization reaction, 40 g of acrylamide, 10 g of methacrylic acid and 0.1 g of 2,2-azobisisobutylonitrile were further added to the reaction system, and the reaction was continued at 60° C. for 24 hours.

The hydrophilic fine gel particles so obtained were spherical particles having a weight-average particle diameter in a water-swollen state of 2.54 μm, a number-average particle diameter of 2.30 μm and a very sharp particle diameter distribution (a weight-average particle diameter/number-average particle diameter ratio = 1.10). The ζ-potential of the particles was −52.0 mV in distilled water.

EXAMPLE 3

Hydrophilic fine gel particles were obtained in the same manner as in Example 1 except that n-butanol was used instead of ethanol.

The hydrophilic fine gel particles so obtained were spherical particles having a weight-average particle diameter in a water-swollen state of 4.35 μm, a number-average particle diameter of 4.14 μm and a monodisperse particle diameter distribution (a weight-average particle diameter/number-average particle diameter ratio = 1.05). The ζ-potential of the particles was −30.3 mV in distilled water.

EXAMPLE 4

Hydrophilic fine gel particles were obtained in the same manner as in Example 1 except that the monomer mixture was composed of 50.9 g of acrylamide, 16.2 g of methylene bisacrylamide, 16.2 g of polyethylene oxide diacrylate (molecular weight: 522) (a product of Nippon Kayaku Co., Ltd.; KAYARAD PEG400DA), 15 g of glycidyl methacrylate and 20 g of methacrylic acid.

The hydrophilic fine gel particles were spherical particles having a weight-average particle diameter in a water-swollen state of 1.64 μm, a number-average particle diameter 1.61 μm and a monodisperse particle diameter distribution (a weight-average particle diameter/number-average particle diameter ratio = 1.02). The ζ-potential of the particles was −24.7 mV in distilled water.

EXAMPLE 5

Spherical hydrophilic fine gel particles were obtained in the same manner as in Example 1 except that there was used a monomer mixture composed of 52 g of acrylamide, 10 g of methyl methacrylate, 30.0 g of methylene bisacrylamide and 8 g of methacrylic acid.

The hydrophilic fine gel particles had a weight-average particle diameter in a water-swollen state of 0.84 μm, a number-average particle diameter of 0.76 μm and a monodisperse particle diameter distribution (a weight-average particle diameter/number-average particle diameter ratio = 1.11). The ζ-potential of the particles was −23.3 mV in distilled water.

COMPARATIVE EXAMPLE 2

Polymerization reaction was carried out in the same manner as in Example 5 except that methyl methacrylate was not used.

The hydrophilic fine gel particles so obtained were spherical particles having a weight-average particle diameter in a water-swollen state of 2.23 μm, a number-average particle diameter of 0.26 μm and a very wide particle diameter distribution (a weight-average particle diameter/number-average particle diameter ratio = 8.58).

EXAMPLE 6

Hydrophilic fine gel particles were obtained in the same manner as in Example 1 except that N,N-dimethylaminoethyl methacrylate (a product of Mitsubishi Rayon Co., Ltd.; ACRYESTER DM) was used instead of glycidyl methacrylate.

The hydrophilic fine gel particles so obtained were spherical particles having a weight-average particle average particle diameter of 1.45 μm and a monodisperse particle diameter distribution (a weight-average particle diameter/number-average particle diameter ratio = 1.14). The ζ-potential of the particles was −42.5 mV in distilled water.

What is claimed is:

1. A process for producing hydrophilic fine gel particles having a particle diameter in a water-swollen state of 0.1–10 μm and a weight-average particle diameter/number-average particle diameter ratio of 1.2 or less, which comprises copolymerizing a monomer mixture of 20–94.8% by weight of a monoethylenically unsaturated amide monomer, 5–60.0% by weight of a crosslinkable ethylenically unsaturated monomer, 0.1–30% by weight of an ethylenically unsaturated carboxylic acid, 0.1–50% by weight of an ester monomer of an acrylic or methacrylic acid, and 0–30% by weight of a monomer copolymerizable with the above-mentioned monomers using a radical polymerization initiator in a solvent which dissolves these monomers but does not dissolve the resulting polymer.

2. A process for producing hydrophilic fine gel particles having a particle diameter in a water-swollen state of 0.1–10 μm and a weight-average particle diameter/number-average particle diameter ratio of 1.2 or less, which comprises copolymerizing a monomer mixture of 20–88% by weight of a monoethylenically unsaturated amide monomer, 10–50% by weight of a crosslinkable ethylenically unsaturated monomer, 2–20% by weight of an ethylenically unsaturated carboxylic acid, 5–40% by weight of an ester monomer of an acrylic or methacrylic acid, and 0–30% by weight of a monomer copolymerizable with the above-mentioned monomers using a radical polymerization initiator in a solvent which dissolves these monomers but does not dissolve the resulting polymer.

3. The process for producing hydrophilic fine gel particles of claims 1 or 2 wherein the solvent which dissolves the monomers but does not dissolve the resulting polymer is a lower alcohol having 6 carbon atoms at most.

4. The process for producing hydrophilic fine gel particles according to claim 1 or 2 wherein said solvent is selected from the group consisting of lower alcohols, tetrahydrofuran, dimethylformamide, dioxane, methyl ethyl ketone, pyridine and dimethylsulfide.

5. The process for producing hydrophilic fine gel particles according to claims 1 to 2 wherein said solvent is mixed with water.

* * * * *